(12) United States Patent
Suzuki

(10) Patent No.: US 9,161,804 B2
(45) Date of Patent: Oct. 20, 2015

(54) TREATMENT INSTRUMENT FOR ENDOSCOPE

(75) Inventor: Keita Suzuki, Tokyo (JP)

(73) Assignee: OLYMPUS CORPORATION (JP)

( * ) Notice: Subject to any disclaimer, the term of this patent is extended or adjusted under 35 U.S.C. 154(b) by 1248 days.

(21) Appl. No.: 13/022,748

(22) Filed: Feb. 8, 2011

(65) Prior Publication Data
US 2011/0137115 A1  Jun. 9, 2011

Related U.S. Application Data

(63) Continuation of application No. PCT/JP2009/003819, filed on Aug. 7, 2009.

(30) Foreign Application Priority Data

Aug. 8, 2008  (JP) ................. P2008-206113

(51) Int. Cl.
*A61B 18/14*  (2006.01)
*A61B 18/00*  (2006.01)
(Continued)

(52) U.S. Cl.
CPC ............. *A61B 18/1445* (2013.01); *A61B 10/06* (2013.01); *A61B 18/1492* (2013.01);
(Continued)

(58) Field of Classification Search
CPC ................ A61B 18/1445; A61B 2018/00946; A61B 2018/00952; A61B 2018/1475; A61B 2017/2929; A61B 2018/00595; A61B 2018/00982; A61B 2017/003; A61B 10/06
USPC .................................................. 606/46, 47
See application file for complete search history.

(56) References Cited

U.S. PATENT DOCUMENTS

2005/0283150 A1* 12/2005 Moutafis et al. ................ 606/49
2008/0125769 A1*  5/2008 Suzuki et al. .................. 606/40

FOREIGN PATENT DOCUMENTS

JP      8-280701     10/1996
JP      9-507149      7/1997
(Continued)

OTHER PUBLICATIONS

International Search Report and Written Opinion mailed Sep. 15, 2009 in corresponding PCT International Application No. PCT/JP2009/003819.

*Primary Examiner* — Michael Peffley
*Assistant Examiner* — Samantha Good
(74) *Attorney, Agent, or Firm* — Ostrolenk Faber LLP

(57) ABSTRACT

This treatment instrument (1) for an endoscope is provided with a treatment section (2) for treatment, an operation wire (2) connected with the treatment section (2), a coil sheath (9) into which the operation wire (3) is inserted, an insulating tube (10) into which the coil sheath (9) is inserted, and an operation section (4) for operating the treatment section (2). The operation section (4) comprises a slider (15) rotatably connected with the operation wire (3), a body (13) to which the slider (15) is mounted movably forward and backward, and a rotational operation section (14) which is so mounted as to be rotatable with respect to the body (13) and has the coil sheath (9) so mounted thereto as to be not rotatable. The distal end of the insulating tube (10) is mounted rotatably and movably forward and backward to the distal end of the coil sheath (9). The proximal end side of the insulating tube (10) is separated in a manner so that the proximal end side is relatively movable in an axial direction with respect to the coil sheath (9) and covered with the operation section (4) so as not to be exposed even when the coil sheath (9) curves.

2 Claims, 5 Drawing Sheets

(51) Int. Cl.
 *A61B 10/06* (2006.01)
 *A61B 17/00* (2006.01)
 *A61B 17/29* (2006.01)
(52) U.S. Cl.
 CPC .. *A61B 2017/003* (2013.01); *A61B 2017/2929* (2013.01); *A61B 2018/00595* (2013.01); *A61B 2018/00982* (2013.01)

(56) References Cited

FOREIGN PATENT DOCUMENTS

JP 2005-34623 2/2005
JP 4056989 3/2008

\* cited by examiner

TREATMENT INSTRUMENT FOR ENDOSCOPE

This application is a continuation of PCT/JP2009/003819, filed Aug. 7, 2009, entitled, "TREATMENT INSTRUMENT FOR ENDOSCOPE". Priority is claimed on Japanese Patent Application No. 2008-206113, filed on Aug. 8, 2008, the contents of which are incorporated herein by reference.

TECHNICAL FIELD

The present invention relates to a treatment instrument for an endoscope which is inserted into a body cavity so as to be used in various kinds of operations.

TECHNICAL BACKGROUND

In recent years, a treatment instrument for an endoscope has been known in which a pair of forceps or the like for gripping a tissue are provided at the distal end of a treatment area (for example, refer to Patent Document 1). When a treatment is performed on a tissue in a body cavity using such forceps or the like, it is necessary to adjust the opening and closing direction of the forceps since the opening and closing direction of the forceps projected into the body cavity is not suitable for the position of a tissue to be treated.

In the treatment instrument for an endoscope described in Patent Document 1, an operation shaft member for opening and closing a pair of forceps is connected to a slider. Additionally, the forceps are fixed to an insertion tube through which an operation shaft member is inserted so as not to be rotatable around the axis, and the proximal end of the insertion tube is fixed to an operation portion.

Accordingly, in a case where the opening and closing direction of the forceps is adjusted, a user rotates the overall operation portion around the axis. Then, the insertion tube rotates around the axis, and finally the forceps rotate around the axis, thereby adjusting the opening and closing direction.

PRIOR TECHNOLOGY DOCUMENTS

Patent Documents

[Patent document 1] Japanese Patent No. 4056989

DISCLOSURE OF THE INVENTION

Problems to be Solved by the Invention

However, in the treatment instrument for an endoscope described in Patent Document 1, the opening and closing direction of the forceps cannot be adjusted if the overall operation portion is not rotated, and replacement of the operation portion becomes necessary in a case where the forceps are intended to be rotated by a predetermined angle or more. Therefore, there is a problem in that the operation becomes complicated.

Additionally, an insertion tube formed from a coil or the like transmits the torque generated by the rotation of the operation portion to the forceps at the distal end. However, since a small-diameter operation shaft member is lower in torque transmissibility compared to an insertion tube, rotational strain occurs due to the difference in transmissibility between both, and accumulates in the operation shaft member. Thereby, there occurs a so-called rotation jump in which the forceps do not follow the rotation of the operation portion favorably, and a rotational strain accumulated in the operation shaft member is released all at once in a location where the operation portion has been rotated to some degree, and thus the forceps rotate by a large angle. Accordingly, as a result, there is also a problem in that fine adjustment of the opening and closing direction of the forceps becomes difficult.

The invention has been made in view of the above, and the object thereof is to provide a treatment instrument for an endoscope which can suitably adjust the direction of a treatment portion with ease without causing a rotation jump or the like.

Means for Solving the Problem

A treatment instrument for an endoscope of the invention includes a treatment portion for performing a treatment on a tissue in a body cavity; an operation wire connected to the proximal end of the treatment portion; a flexible coil sheath through which the operation wire is inserted; an insulating cladding tube through which the coil sheath is inserted; and an operation portion for operating the treatment portion. The operation portion has an advance and retract operation portion having the proximal end of the operation wire connected thereto so as to be rotatable around an axis, a main body to which the slider is attached so as to be capable of advancing and retracting in the direction of the axis, and a rotational operation portion attached to the main body so as to be rotatable around the axis and having the proximal end of the coil sheath attached thereto so as not to be rotatable around the axis. The distal end of the cladding tube is attached to the distal end of the coil sheath so as to be rotatable around the axis and incapable of advancing and retracting in the direction of the axis, and the proximal side of the cladding tube is separated so as to be movable in the direction of the axis relative to the coil sheath and covered with a predetermined length or more of the operation portion so that the coil sheath is not exposed even if the coil sheath curves.

The proximal end of the operation wire may be connected to the advance and retract operation portion so as to be rotatable around the axis, using a ball-bearing made of an electric conductor, the advance and retract operation portion may have a plug for connection with a power source, and the plug may be conducted to the operation wire via the ball-bearing.

In this case, while releasing the rotational strain accumulated in the operation wire, a reliable conduction between the plug and the operation wire can be achieved, and the treatment portion can perform various kinds of treatment.

Effects of the Invention

As described above, according to the treatment instrument for an endoscope of the invention, the direction of the treatment portion can be suitably regulated with ease without causing a rotation jump or the like of the treatment portion.

EMBODIMENTS FOR IMPLEMENTING THE INVENTION

Preferred embodiments of the invention will now be described below with reference to the drawings. A treatment instrument for an endoscope of a first embodiment of the invention will be described below with reference to FIGS. 1 to 4.

[First Embodiment]

Figure 1:
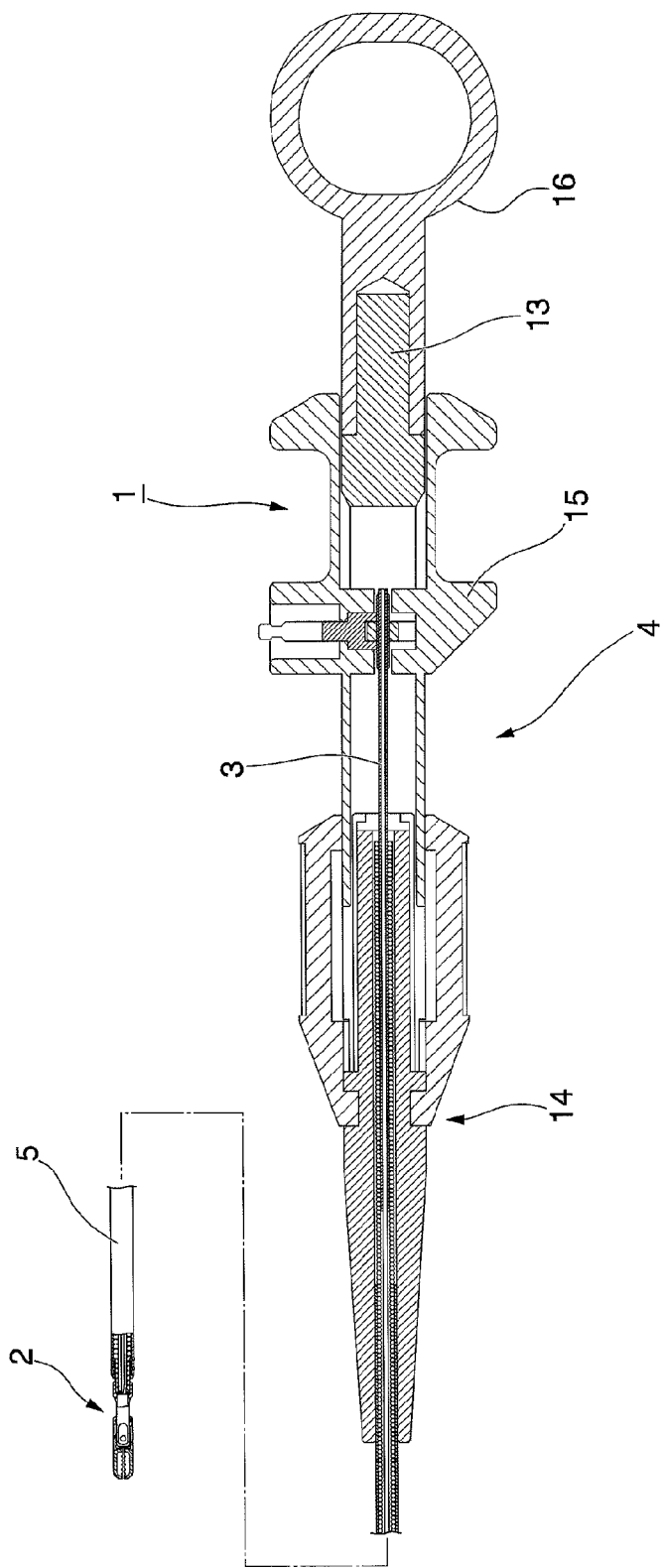
FIG. 1 is an overall view of a treatment instrument for an endoscope of a first embodiment of the invention.

As shown in FIG. 1, a treatment instrument (hereinafter referred to as a "treatment instrument") 1 for an endoscope of the present embodiment includes a treatment portion 2 for performing a treatment on a tissue in a body cavity, an operation wire 3 connected to the proximal end of the treatment portion 2, an operation portion 4 connected to the operation wire 3 for operating the treatment portion 2, and an insertion portion 5 for connecting the treatment portion 2 with the operation portion 4.

Figure 2:
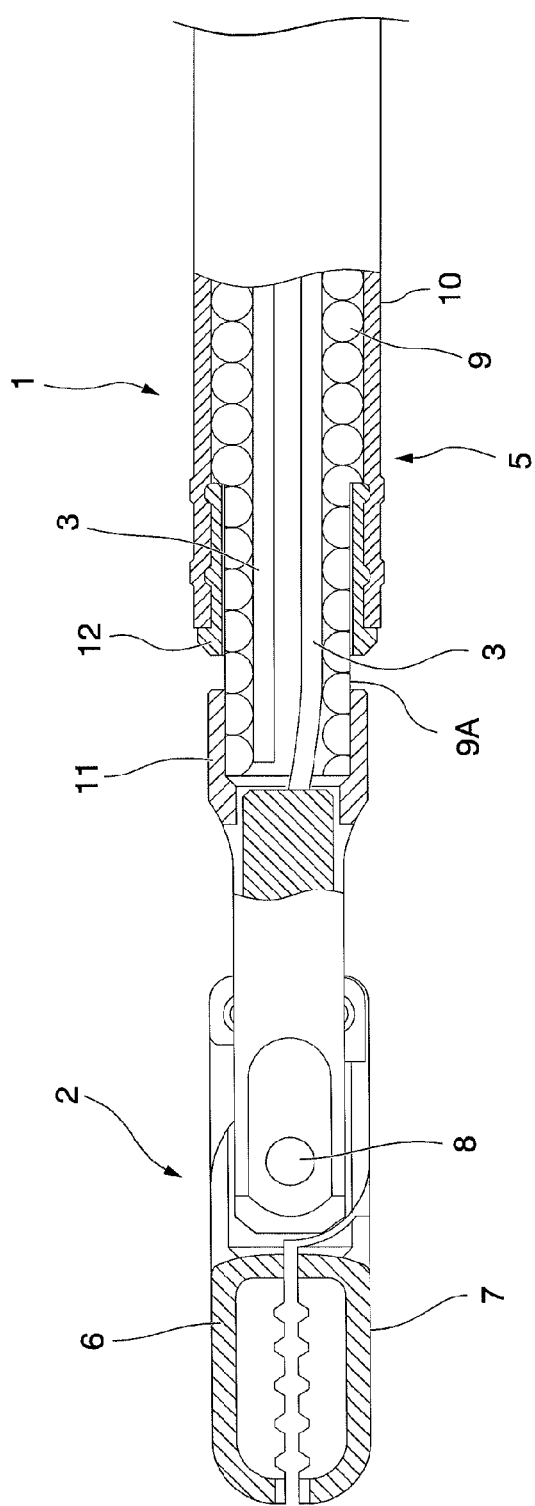
FIG. 2 is an enlarged sectional view of the distal side of the treatment instrument for an endoscope.

FIG. 2 is an enlarged sectional view of a tip portion of the treatment instrument 1 including the treatment portion 2. The treatment portion 2 is constructed so that a pair of forceps members which consist of a first forceps member 6 and a second forceps member 7 are rotatably connected to each other by a turning shaft 8. The operation wire 3 is connected to the portion of each of the forceps members 6 and 7 closer to the proximal side than the turning shaft 8 and is connected to the operation portion 4 through the inside of the insertion portion 5.

The insertion portion 5 includes a coil sheath 9, and an insulating tube (cladding tube) 10 which covers the periphery of the coil sheath 9.

The coil sheath 9 is formed by densely winding a metal element wire in the shape of a loop, and transmits the operation for rotating the treatment portion 2 to the treatment portion 2. Whether the construction of the coil sheath 9 is made to be of a single strip type in which one metal element wire is wound, or a multi-strip type in which a plurality of metal element wires is wound, and made to be of a single layer type in which an element wire is not wound overlappingly in the radial direction or a multilayer type in which an element wire is wound overlappingly plural times may be appropriately determined according to the characteristics required for the coil sheath 8 in view of the applications or the like of the treatment instrument 1.

A cover 11 for fixing the treatment portion 2 is attached to the distal end of the coil sheath 9, and the turning shaft 8 and the coil sheath 9 are integrally connected by the cover 11. Therefore, the turning shaft 8 to be relatively immovable in the direction of an axis of the coil sheath 9.

The insulating tube 10 is formed from an insulating material and covers the outer surface of the coil sheath 9. A substantially cylindrical engaging member 12 is attached to the distal end of the insulating tube 10 by press-fitting or the like. The engaging member 12 engages with an engaging groove 9A formed in a circumferential direction near the distal end of the coil sheath 9.

By adopting such a construction, the distal end of the insulating tube 10 is attached to the coil sheath 9 so as to be rotatable around an axis and relatively immovable in the direction of the axis.

Figure 3:
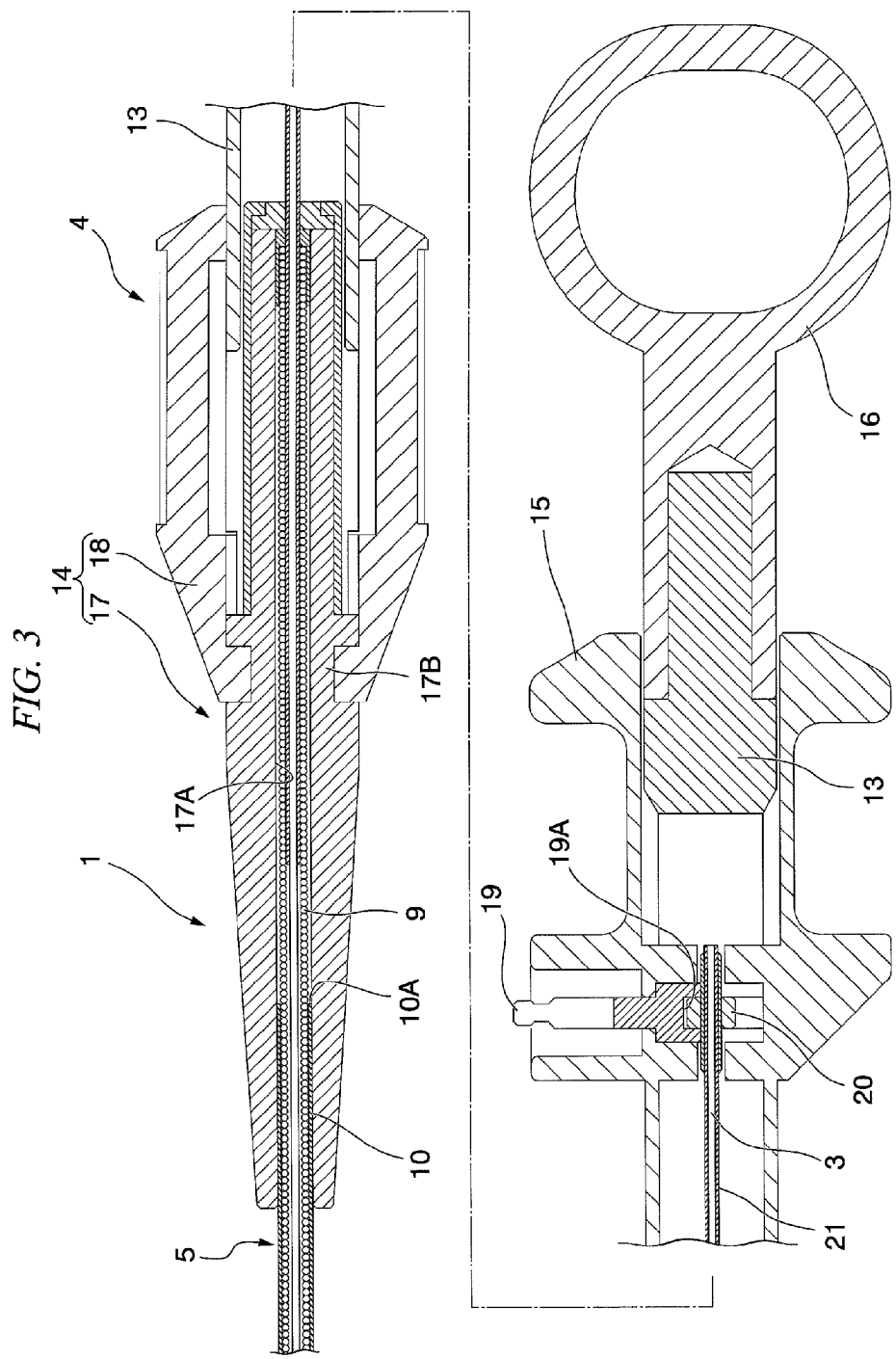
FIG. 3 is an enlarged sectional view of an operation portion of the treatment instrument for an endoscope.

FIG. 3 is an enlarged sectional view of the operation portion 4. The operation portion 4 includes an elongated main body 13, a rotational operation portion 14 attached to the main body 13 so as to be rotatable around the axis, and a slider (advance and retract operation portion) 15 attached to the main body 13 so as to be slidable within a certain range in the direction of the axis.

The main body 13 has a space therein, such as a groove or a slit, which can receive the operation wire 3 and a region on the proximal side of the insertion portion 5. A handle 16 for finger hooking is provided at the proximal end of the main body 13.

The rotational operation portion 14 consists of a tubular member 17 through which the proximal side of the insertion portion 5 is inserted, and a dial member 18 attached to the tubular member 17.

The tubular member 17 is formed with a through-hole 17A extending in the direction of the axis, and a region on the proximal side of the insertion portion 5 is inserted into the through-hole 17A. Also, the proximal end of the coil sheath 9 is connected and fixed to the proximal side of the tubular member 17 so as not to be rotatable around the axis with respect to the tubular member 17.

Meanwhile, the proximal side of the insulating tube 10 is inserted into the through-hole 17A by a predetermined length, for example, about 30 mm, and is covered with the operation portion 4. Also, the proximal end 10A of the insulating tube 10 is located closer to the distal side of the coil sheath 9 than the proximal end thereof, and is brought into a state where the proximal end is separated from the tubular member 17 and the coil sheath 9 without being fixed to either the tubular member or coil sheath. This causes the proximal end 10A to be movable in the direction of the axis with respect to the coil sheath 9. The behavior of the proximal end 10A when the treatment instrument 1 is used will be described below.

Although the dial member 18 is attached so as to become substantially coaxial with the tubular member 17, since a cross-section which goes straight in the direction of the axis of the tubular member 17 is formed substantially in the shape of a square at a connection part 17B between the tubular member 17 and the dial member 18, both the members are made not to be rotatable relative to each other. Accordingly, when the dial member 18 is rotationally operated around the axis, the tubular member 17 also rotates around the axis in an interlocking manner. As a result, the overall rotational operation portion 14 rotates around the axis.

A plug 19 for connection of a power cable (not shown) connected to a high-frequency power source (not shown) is attached to the slider 15. The end of the plug 19 located inside the main body 13 is formed with a rotational groove 19A which extends in the direction of the axis of the plug 19.

A substantially disk-shaped rotary plate 20 is arranged in the rotational groove 19A. A tube 21 for preventing buckling of the operation wire 3 is fixed to the rotary plate 20 so as to become coaxial with the rotary plate 20. The proximal end of the operation wire 3 which has extended through the proximal end of the tubular member 17 is inserted into the tube 21 and integrally fixed to the tube 21 by brazing or the like.

With this construction, the proximal end of the operation wire 3 is connected to the slider 15 via the tube 21 and the rotary plate 20 so as to be rotatable around the axis.

The operation when the treatment instrument 1 constructed as described above is used will be described.

First, a user inserts an endoscope (not shown) into a patient's body, and advances the distal end of the endoscope to the vicinity of a tissue in a body cavity to be treated.

Subsequently, the user moves the slider 15 backward with respect to the main body 13, thereby bringing the treatment portion 2 into a closed state, and inserts the treatment portion 2 and insertion portion 5 of the treatment instrument 1 into a forceps channel (not shown) of the endoscope. Then, after the treatment portion 2 is projected from the forceps channel, the high-frequency power source and the plug 19 are connected to the power cable.

When a treatment is performed, the slider 15 is advanced with respect to the main body 13. Then, the operation wire 3 connected to the slider 15 advances with respect to the coil sheath 9. As described above, since the turning shaft 8 is immovable relative to the insertion portion 5, the first forceps member 6 and the second forceps member 7 turn about the turning shaft 8, respectively, and the treatment portion 2 opens.

When the user opens the treatment portion 2 to locate a target tissue between the forceps members 6 and 7, and pulls the slider 15 back to the proximal side of the main body 13, the distal sides of the forceps members 6 and 7 are closed again, and the target tissue is nipped by the treatment portion 2.

In this state, when the user supplies a high-frequency current from the high-frequency power source, the high-frequency current is supplied from the plug 19 through the operation wire 3 to the treatment portion 2, and the target tissue is cauterized by the high-frequency current.

Thereafter, the user removes the high-frequency treatment instrument 1 from the forceps channel, and removes the endoscope to the outside of the body and ends the treatment.

Although the above is the operation in normal use of the treatment instrument 1, in a case where the direction of opening and closing of the forceps members 6 and 7 of the treatment portion 2 projected from the forceps channel is not fitted to a tissue to be treated, the treatment by the treatment portion 2 cannot be appropriately performed. In such a case, the user performs the adjustment operation of operating the rotational operation portion 14 to rotate the treatment portion 2 around the axis. The operation of individual sections of the treatment instrument 1 in this adjustment operation will now be described below.

In a case where the adjustment operation is performed, the user rotates the dial member 18 of the rotational operation portion 14 toward a desired direction around the axis. Then, the tubular member 17, and the coil sheath 9, which is attached to the tubular member 17 so as not to be relatively rotatable, rotate in the same direction as the dial member 18 in an interlocking manner.

When the coil sheath 9 rotates, the treatment portion 2 integrated with the coil sheath 9 by the cover 11 rotates, so that the direction of opening and closing of the forceps members 6 and 7 can be adjusted.

At this time, although the operation wire 3 connected to the proximal end of the treatment portion 2 also rotates with the rotation of the treatment portion 2, since the torque transmission performance of the operation wire 3 is low compared to the coil sheath 9, a rotational strain easily accumulates in the operation wire 3.

However, since the proximal end of the operation wire 3 is rotatably connected to the plug 19 of the slider 15 via the tube 21 and the rotary plate 20, the accumulated rotational strain is released as needed at this proximal end, thereby preventing a rotation jump from occurring.

Additionally, since the treatment instrument 1 is inserted through the forceps channel of the endoscope in rotational operation, the insulating tube 10 is fixed to the inner wall of the forceps channel so as not to be substantially relatively rotatable by a frictional force generated between the insulating tube and the inner wall. However, since the distal end of the insulating tube 10 is attached to the coil sheath 9 so as not to be relatively rotatable, even if the insulating tube 10 is fixed to the forceps channel as described above, the fixed state does not affect the rotational operation of the treatment portion 2 via the coil sheath 9.

Figure 4:
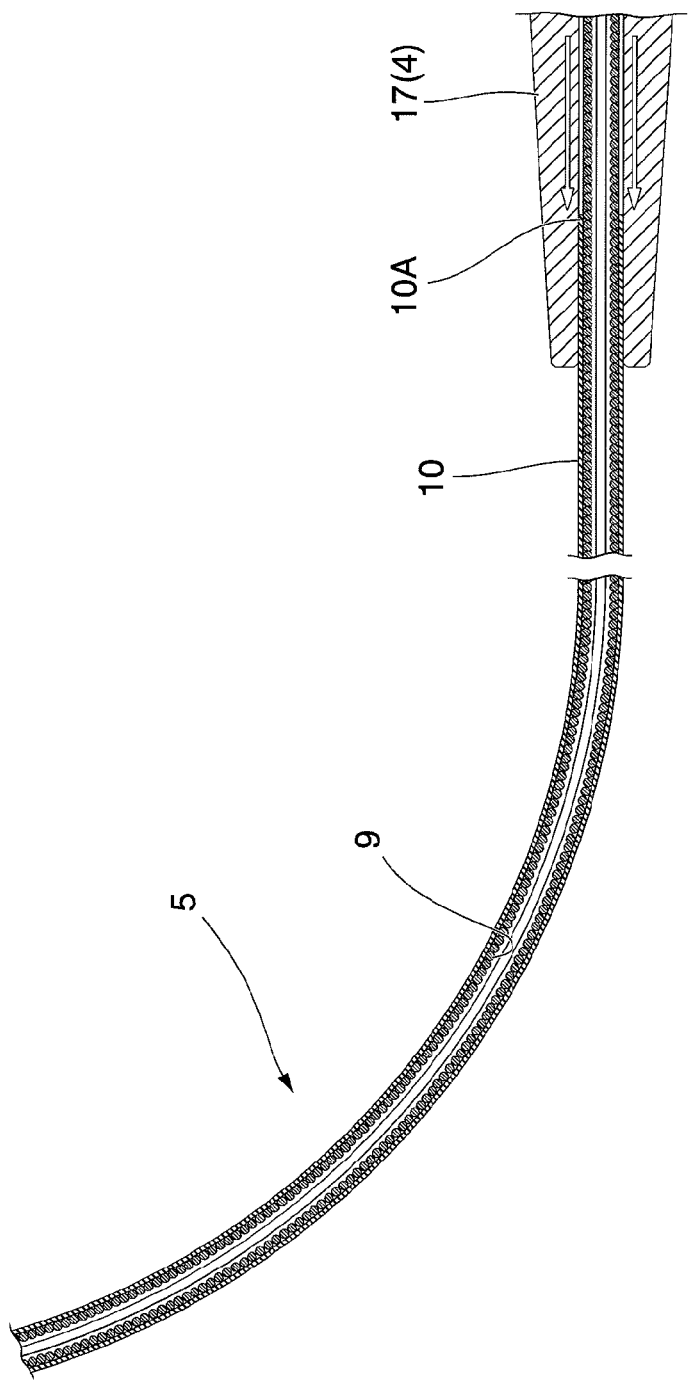
FIG. 4 is a view showing the operation when the treatment instrument for an endoscope is used.

Moreover, the proximal end 10A of the insulating tube is brought into a separated free state without being fixed to the tubular member 17 or the coil sheath 9. Accordingly, as shown in FIG. 4, when the coil sheath 9 is curved, for example, by the endoscope meandering within a body cavity, the proximal end 10A moves to the distal side in accordance with deformation of the coil sheath 9 accompanying the curving. When the proximal end 10A is fixed to the tubular member 17 or the coil sheath 9, the insulating tube 10 is compressed or extended in the direction of the axis by the deformation of the coil sheath 9 accompanying the curving. This is one cause of deterioration of flexibility or occurrence of a rotation jump. However, the compression and extension of the insulating tube 10 are appropriately suppressed as the proximal end 10A is brought into a free state.

According to the treatment instrument 1 of the present embodiment, by the cooperation of the above-described individual effects, adjustment of the direction of the treatment portion 2 can be appropriately performed by operating the rotational operation portion 14 to rotate the treatment portion 2 by a desired amount of rotation reliably, while suppressing the occurrence of a rotation jump caused by a rotational strain being accumulated in the operation wire 3.

Additionally, the proximal end 10A of the insulating tube 10 of the insertion portion 5 is inserted into the tubular member 17 of the operation portion 4 by a predetermined length, and a certain range of the region on the side of the proximal end 10A of the insulating tube 10 is covered with the operation portion 4. Accordingly, as shown in FIG. 4, even if the insertion portion 5 curves and the proximal end 10A moves to the distal side, the conductive outer surface of the coil sheath 9 is not exposed, and an insulated state can be maintained more reliably.

Although an example of the treatment instrument in which the plug 19 is provided and the treatment portion 2 is powered has been described in the present embodiment, the invention can also be applied to a treatment instrument in which the treatment portion is powered. That is, by forming a shape equivalent to the rotational groove 19A in a portion of the slider 15, thereby arranging the rotary plate 20, without providing the slider 15 with the plug 19, the above-described effects can be similarly obtained even in the treatment instrument in which the treatment portion is not powered.

[Embodiment 2]

Next, a second embodiment of the invention will be described with reference to FIG. 5. The difference between the treatment instrument 31 of the present embodiment and the above-described treatment instrument 1 is a connection mode between the operation wire and the slider.

In addition, constituent elements common to those of the treatment instrument 1 of the first embodiment will be designated by the same reference numerals, and the description thereof is omitted.

Figure 5:
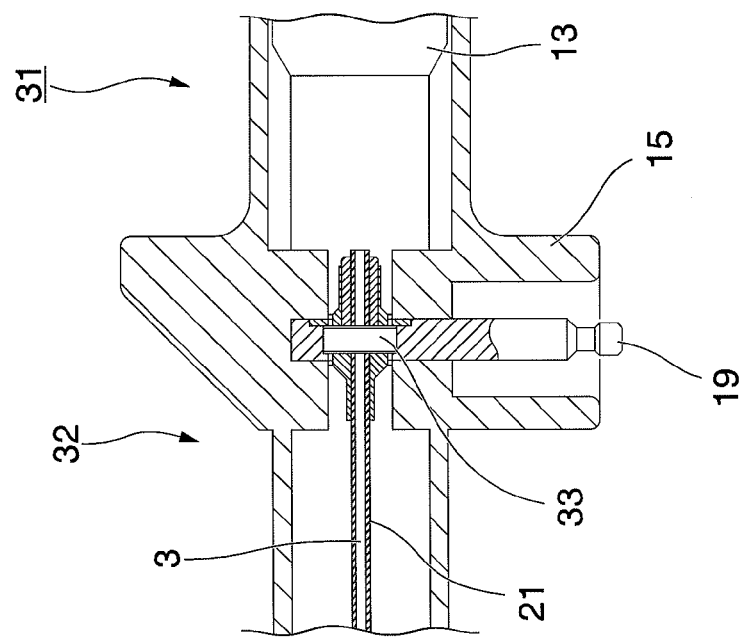
FIG. 5 is a partially enlarged sectional view showing an operation portion of a treatment instrument for an endoscope of a second embodiment of the invention.

FIG. 5 is a partially enlarged sectional view of the operation portion 32 of the treatment instrument 31. The tube 21 and the plug 19 are relatively rotatably connected together via a ball bearing 33.

Although a ball bearing with a well-known construction can be adopted as the ball bearing 33, since the plug 19 and the operation wire 3 can be electrically connected together via the ball bearing 33, all members containing balls (not shown) may be formed from electric conductors, such as stainless steel.

In addition, in this case, in order to provide good conduction, it is not necessary to apply grease for increasing lubricity to the balls. Typically, since the amount of rotation of the ball bearing 33 accompanying the rotational operation of the treatment instrument 2 is significantly small compared to a general ball bearing, there is no problem even if grease is not applied if the surfaces of individual members which constitute the ball bearing 33 are sufficiently smoothly worked.

Even in the treatment instrument 31 of the present embodiment, the same effects as those of the above-described treatment instrument 1 can be obtained.

Additionally, since the operation wire 3 and the plug 19 of the slider 15 are connected together via the ball bearing 33, the relative rotation of both the operation wire and the plug becomes smoother, and the rotational strain accumulated in the operation wire 3 can be more appropriately released.

Although the individual embodiments of the invention have been described, the technical scope of the invention is not limited to the above embodiments, but various modifications may be made without departing from the spirit and scope of the invention.

For example, although an example in which the treatment portion consists of a pair of forceps members has been described in the above-described embodiments, the treatment portion in the treatment instrument of the invention is not limited thereto. That is, if treatment portions which are needed to adjust a direction with respect to a tissue to be treated are provided, the invention can be applied to all treatment portions, such as a snare wire, so-called two-legged forceps, and the like.

INDUSTRIAL APPLICABILITY

As described above, according to the treatment instrument for an endoscope of the invention, the direction of the treatment portion can be suitably adjusted with ease without causing a rotation jump or the like of the treatment portion. Additionally, the treatment portion can be rotated by rotating the rotational operation portion without rotating the main body. Moreover, the rotational strain accumulated in the operation wire by a rotational operation can be appropriately released as needed since the proximal end of the operation wire is rotatably connected to the advance and retract operation portion, and the proximal side of the cladding tube is separated so as to become movable in the direction of the axis relative to the coil sheath.

DESCRIPTION OF THE REFERENCE NUMERALS 1, 31: Treatment instrument for endoscope
2: Treatment portion
3: Operation wire
4, 32: Operation portion
9: Coil sheath
10: Insulating tube (Cladding tube)
13: Main body
14: Rotational operation portion
15: Slider (Advance and retract operation portion)
33: Ball bearing

What is claimed is:

1. A treatment instrument for an endoscope comprising:
    a treatment part configured to perform a treatment on a tissue in a body cavity;
    an operation wire connected to a proximal end of the treatment part, the operation wire extending along an axis;
    a flexible coil sheath through which the operation wire is inserted;
    an insulating cladding tube through which the coil sheath is inserted; and
    an operation part configured to operate the treatment part, wherein the operation part has:
        an advance and retract operation part to which a proximal end of the operation wire is connected such that the proximal end of the operation wire is rotatable around the axis relative to the advance and retract operation part;
        a main body to which the advance and retract operation part is attached such that the advance and retract operation part is capable of advancing and retracting along the axis relative to the main body; and
        a rotational operation part attached to the main body such that the rotational operation part is rotatable around the axis relative to the main body, a proximal end of the coil sheath being attached to the rotational operation part such that the proximal end of the coil sheath is incapable of rotating around the axis relative to the rotational operation part, and
    wherein a distal end of the cladding tube is attached to a distal end of the coil sheath such that the distal end of the cladding tube is rotatable around the axis relative to the distal end of the coil sheath and is incapable of advancing and retracting along the axis relative to the distal end of the coil sheath, and a proximal side of the cladding tube is separated from the coil sheath such that the proximal side of the cladding tube is capable of advancing and retracting along the axis relative to the coil sheath and the proximal side of the cladding tube is covered with the operation part having a length equal to or greater than a predetermined length so that the coil sheath is not exposed when the coil sheath curves.

2. The treatment instrument for an endoscope according to claim 1,
    wherein the proximal end of the operation wire is connected to the advance and retract operation part so as to be rotatable around the axis, using a ball bearing made of an electric conductor, the advance and retract operation part has a plug for connection with a power source, and the plug is conducted to the operation wire via the ball bearing.

* * * * *